(12) United States Patent
McKnight et al.

(10) Patent No.: US 11,584,919 B2
(45) Date of Patent: Feb. 21, 2023

(54) COMPOSITION FOR DETECTING ALPHA PARTICLE RADIATION AND METHODS OF USE

(71) Applicant: UT-Battelle, LLC, Oak Ridge, TN (US)

(72) Inventors: Timothy E. McKnight, Greenback, TN (US); David E. Graham, Knoxville, TN (US); Robert F. Standaert, Knoxville, TN (US); Linda A. Lewis, Andersonville, TN (US); Samuel A. Lewis, Andersonville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 388 days.

(21) Appl. No.: 16/748,039

(22) Filed: Jan. 21, 2020

(65) Prior Publication Data

US 2020/0231951 A1 Jul. 23, 2020

Related U.S. Application Data

(60) Provisional application No. 62/795,118, filed on Jan. 22, 2019.

(51) Int. Cl.
*C12N 9/16* (2006.01)
*G01T 7/00* (2006.01)
(Continued)

(52) U.S. Cl.
CPC ............ *C12N 9/16* (2013.01); *C12P 7/625* (2013.01); *C12Q 1/44* (2013.01); *G01K 11/12* (2013.01);
(Continued)

(58) Field of Classification Search
CPC .. C12N 9/16; C12N 9/20; C12P 7/625; G01K 11/12; G01N 21/6428; G01N 2021/6439; G01T 1/1606; G01T 7/00; G01T 1/178
(Continued)

(56) References Cited

U.S. PATENT DOCUMENTS

| 5,002,768 A * | 3/1991 | Kondo ............ A01N 25/28 514/963 |
| 2003/0113368 A1* | 6/2003 | Nomoto ............ A61K 9/5073 435/135 |

(Continued)

OTHER PUBLICATIONS

Jacobson, D.R. et al., "Measurement of radon and xenon binding to a cryptophane molecular host", Proc Natl Acad Sci USA, 108(27): 10969-10973 (Jul. 5, 2011).
(Continued)

*Primary Examiner* — David P Porta
*Assistant Examiner* — Gisselle M Gutierrez
(74) *Attorney, Agent, or Firm* — Scully, Scott, Murphy & Presser, P.C.

(57) ABSTRACT

A capsule composition comprising: (a) a polyester shell having a thickness of no more than 20 microns, and (b) a solution containing a visual and/or olfactory indicator, wherein the solution is encapsulated by the polyester shell. Also described herein is a method for detecting alpha particle radiation, in which: (i) the capsule composition is placed in contact with an esterase in a location where the presence of alpha particle radiation is being determined; (ii) waiting a period of time for the esterase to degrade the polyester shells, wherein the period of time is insufficient for the esterase to cause leakage of the solution in the absence of alpha particle radiation but is sufficient for alpha particle radiation, if present, to cause leakage from the capsule composition; and (iii) observing whether leakage has
(Continued)

occurred at the end of the period of time to determine whether alpha particle radiation is present.

24 Claims, 7 Drawing Sheets

(51) Int. Cl.
    *G01T 1/16*      (2006.01)
    *G01K 11/12*      (2021.01)
    *G01N 21/64*      (2006.01)
    *C12P 7/625*      (2022.01)
    *C12Q 1/44*      (2006.01)

(52) U.S. Cl.
    CPC ....... *G01N 21/6428* (2013.01); *G01T 1/1606* (2013.01); *G01T 7/00* (2013.01); *G01N 2021/6439* (2013.01)

(58) Field of Classification Search
    USPC .......................................................... 378/207
    See application file for complete search history.

(56) References Cited

U.S. PATENT DOCUMENTS

| | | | | |
|---|---|---|---|---|
| 2005/0031847 A1* | 2/2005 | Martens | ................. | C11D 3/201 |
| | | | | 428/411.1 |
| 2005/0048856 A1* | 3/2005 | Hauser | ................. | A61K 8/375 |
| | | | | 427/393.1 |
| 2006/0154834 A1* | 7/2006 | Hauser | ................. | A61Q 19/00 |
| | | | | 510/119 |
| 2006/0159924 A1* | 7/2006 | Hauser | ................. | A61K 8/0208 |
| | | | | 428/411.1 |
| 2006/0222686 A1* | 10/2006 | Hauser | ................. | A61K 9/0014 |
| | | | | 424/443 |
| 2006/0233866 A1* | 10/2006 | Hauser | ..................... | A61K 8/92 |
| | | | | 424/443 |
| 2020/0231951 A1* | 7/2020 | McKnight | ............. | G01T 1/1606 |

OTHER PUBLICATIONS

Kang, H. M. et al., "Effect of Solubility and Miscibility on the Adhesion Behavior of Polymer-Coated Carbon Fibers with Vinyl Ester Resins", Journal of Applied Polymer Science, 79:1042-1053 (2001).

Kemme, M. et al., "Comparative study on the enzymatic degradation of poly (lactic-co-glycolic acid) by hydrolytic enzymes based on the colorimetric quantification of glycolic acid", Polymer Testing, 30, pp. 743-748 (2011).

Laureano-Perez et al., "A Novel Application for 222Rn Emanation Standards: Radon-cryptophane host chemistry", Applied Radiation and Isotopes, 70(9), pp. 1997-2001, (Sep. 2012).

McCall, R.L. et al., "PLGA Nanoparticles Formed by Single-or Double-emulsion with Vitamin E-TPGS", Journal of Visualized Experiments, 82, e51015, pp. 1-8 (Dec. 2013).

Ng, S.M. et al., "A review on fluorescent inorganic nanoparticles for optical sensing applications", The Royal Society of Chemistry, vol. 6, pp. 21624-21661 (2016).

Yang, H. et al., "Comparison of Unsaturated Polyester and Vinylester Resins in Low Temperature Polymerization", Applied Polymer, 79(7), 1230-1242 (2001).

* cited by examiner

COMPOSITION FOR DETECTING ALPHA PARTICLE RADIATION AND METHODS OF USE

CROSS REFERENCE TO RELATED APPLICATION

The present application claims benefit of U.S. Provisional Application No. 62/795,118, filed on Jan. 22, 2019, all of the contents of which are incorporated herein by reference.

GOVERNMENT SUPPORT

This invention was made with government support under Prime Contract No. DE-AC05-00OR22725 awarded by the U.S. Department of Energy. The government has certain rights in the invention.

FIELD OF THE INVENTION

The present invention relates generally to methods and devices for detecting alpha particle radiation and more particularly, to compositions and methods for visual detection of such radiation.

BACKGROUND OF THE INVENTION

A variety of handheld and laboratory instruments have been developed for detecting and measuring radiation, including Geiger counters, sodium iodide detectors, ionization chambers, liquid scintillation counters, and multichannel analyzers. These are generally costly, require complex electronics, and typically require operators to be in close proximity to potentially hazardous levels of alpha particle radiation for unsafe periods of time. For the on-site detection of alpha-particle radiation, end window Geiger tubes generally must be held close to the source of contamination, and they typically do not distinguish between alpha- and beta-radiation. Conventional practice is for radiological technicians to survey radiological areas by standing close with either handheld instruments or by obtaining 'swipes' of surfaces and conducting analyses of the transferable contamination removed by the swipe. This process forces the technician to interact with potential contamination and increases the risk to radiation workers and to the facility and environment by the possibility of transferring the contamination to even wider distributions. Thus, there would be a significant advantage in a method for detecting alpha particle radiation that is low cost, relies on straight-forward sensory observation, and does not require operators to be in close proximity to radioactive sources for unsafe periods of time.

SUMMARY OF THE INVENTION

In one aspect, the present invention is directed to a capsule composition containing a visual or olfactory indicator, wherein the capsules possess the property of leaking the visual or olfactory indicator only when exposed to alpha particle radiation. The capsules have the following composition: (a) a polyester shell having a thickness of no more than 20 microns, and (b) a solution containing a visual or olfactory indicator, wherein the solution is encapsulated by the polyester shell. The polyester may be, for example, a polyhydroxyalkanoate, such as polylactic acid, polyglycolic acid, poly(3-hydroxypropionic acid), poly(hydroxybutyric acid)s, poly(hydroxyvaleric acid)s, poly(hydroxyhexanoic acid)s, polycaprolactone, polymandelic acid, or copolymer thereof. The visual indicator may be, for example, a fluorophore or a non-fluorophore dye. The olfactory indicator may be, for example, an amine compound, mercaptan compound, plant-derived scent, perfume, or subtle scent detectable by sniffer dogs.

In another aspect, the invention is directed to a method for detecting alpha particle radiation using the above described capsule composition. In brief, the method operates by contacting the above described capsule composition with an esterase (polyester shell etchant) in a location where alpha particle radiation is suspected, wherein the esterase is capable of etching the polyester shell, thereby causing its ultimate degradation and leakage of the internal solution. Alpha particle radiation, if such radiation is present, initiates chemically reactive defect sites within the polyester shell which facilitates more rapid etching by the esterase. The enhanced etching caused by alpha particle radiation results in leakage of the capsules in much shorter time than would be possible by the esterase alone. Thus, by this method, alpha particle radiation can be determined to be present if leakage of the indicator solution from the capsules is observed to occur in a shorter time period than is known to occur from the esterase alone (i.e., in the absence of alpha particle radiation) over the same time period.

In some embodiments, the method more particularly includes the following steps: (i) placing a capsule composition and an esterase in contact with each other in a location where the presence of alpha particle radiation is being determined, wherein the capsule composition includes: (a) polyester shells having a thickness of no more than 20 microns, and (b) a solution containing a visual or olfactory indicator, wherein the solution is encapsulated by the polyester shells; (ii) waiting a period of time for the esterase to degrade the polyester shells, wherein the period of time is insufficient for the esterase to cause leakage of the solution from the capsule composition in the absence of alpha particle radiation, while the same period of time is sufficient for alpha particle radiation, if present, to facilitate degradation of the polyester shells to the extent that leakage from the capsule composition would occur; and (iii) observing whether leakage from the capsule composition occurs at the completion of the period of time to determine whether alpha particle radiation is present.

In further embodiments, the method more particularly includes the following steps: (i) placing the above-described capsule composition and an esterase in contact with each other in a location where the presence of alpha particle radiation is being determined, wherein the capsule composition includes: (a) polyester shells having a thickness of no more than 20 microns, and (b) a solution containing a visual or olfactory indicator, wherein the solution is encapsulated by the polyester shells; (ii) waiting a period of time for the esterase to initiate low-level defects in the polyester shells without causing leakage of the capsule composition, and waiting a further period of time during which the esterase is incapable of etching the polyester shells to the extent that leakage from the capsule composition would occur, while the further period of time is also sufficient for alpha particle radiation, if present, to etch the polyester shells to the extent that leakage from the capsule composition would occur; and (iii) observing whether leakage from the capsule composition occurs at the completion of the further period of time to determine whether alpha particle radiation is present.

In other embodiments, the method more particularly includes the following steps: (i) placing the above-described capsule composition and an esterase in contact with each other in a location where the presence of alpha particle radiation is being determined, wherein the capsule composition comprises: (a) polyester shells having a thickness of no more than 20 microns, and (b) a solution containing a visual or olfactory indicator, wherein the solution is encapsulated by the polyester shells; (ii) waiting a period of time for the esterase to degrade the polyester shells to an extent that the solution within the capsules leaks out of at least a portion of the capsules; (iii) detecting the leaked visual or olfactory indicator to determine the extent of leakage of the solution; and (iv) comparing the extent of leakage in step (iii) with the extent of leakage in a control experiment under the same conditions except that alpha particle radiation is known not to be present, wherein, if the extent of leakage observed in step (iii) is determined to be greater than the extent of leakage of the control, alpha particle radiation is determined to be present.

The above described methods advantageously permit crews to precisely locate sources of alpha radiation contamination within a facility in a safe and straight-forward manner. In some embodiments, the above described method is practiced by deploying a biodegradable aerosolized indicator system containing the capsule composition and esterase (etchant). In other embodiments, the above described method is practiced by placing (e.g., affixing) the capsule composition and esterase etchant on a sheet substrate material when placed in a location where the presence of alpha particle radiation is being determined. The above described approach advantageously relies on polymeric, biodegradable capsules filled with visual (e.g., fluorescent or dye) or olfactory indicators that can be enzymatically released over short time periods under dry, ambient air laboratory conditions, and this release is enhanced by exposure of these capsules to alpha particle radiation. This system provides a novel means of safely and accurately visualizing the precise locations of alpha contamination within a facility, providing safer, faster, and more effective planning and execution of decontamination operations.

In some embodiments, the above described method is particularly directed to the detection of radon. In embodiments where the presence of radon is being tested, the method may further include, before step (i), placing an absorbent material that absorbs radon yet does not block alpha particle emission in a location where the presence of radon is being determined, and, in step (i), placing the capsule composition and esterase in contact with each other on the absorbent material after the absorbent material is provided sufficient time to absorb radon. In more particular embodiments, the method may further include, before step (i), placing an absorbent material that absorbs radon yet does not block alpha particle emission on selective portions of a substrate to result in regions of the substrate containing the absorbent material and regions of the substrate not containing the absorbent material, and placing the substrate in a location where the presence of radon is being determined, and, in step (i), placing the capsule composition and esterase in contact with each other on the regions containing the absorbent material and the regions not containing the absorbent material after the absorbent material is provided sufficient time to absorb radon; proceeding with step (ii); and in step (iii), determining the presence of (or extent of) leakage of the solution in regions containing the absorbent material and comparing this result to regions not containing the absorbent material to determine if regions containing the absorbent material exhibit leakage (or a higher leakage) of the solution compared to regions not containing the absorbent material. In particular embodiments, the absorbent material is or includes a cryptophane material.

In the above described method for detection of radon, the alpha radiation emitted by the radon captured within the absorbent layer will emit in all directions. Thus, in some embodiments, the radon absorbent material is sandwiched between layers of the capsule composition to maximize interaction of radon alpha particle radiation with the capsules, thereby resulting in an improved measurement sensitivity of the device. Further, all radon daughter products will remain captured within the sandwiched layer, and their alpha emissions will also be forced to interact with the indicating capsule layer. Ideally, the top and bottom capsule layers should be of a thickness such that each alpha emission travels through multiple capsules, thereby promoting the release of measurable amounts of capsule fill material. For example, with PLGA microcapsules that are 300 nm in diameter, a 20 micron-thick capsule layer would provide alpha traversal of approximately 60-70 capsules for alpha emissions oriented perpendicular to the planar surface of the detector.

BRIEF DESCRIPTION OF THE FIGURES

FIG. 1 is a plot showing release of fluorescent dye from PLGA microcapsules exposed over extended time periods to lipase derived from *Rhizopus oryzae*, potassium phosphate buffer at pH 8.0, and Tween® 20. Microcapsules and enzyme mixture was co-deposited upon Durx® 770 fabric and incubated at temperatures of 20-23° C. at relative humidity of approximately 40%.

FIG. 2 is a photograph showing dye release from PLGA capsules immobilized onto Durx® 770 clean room wipes and maintained under dry (RH 40%) laboratory conditions (20-23° C.). At top, the capsules were not exposed to enzyme degradation, resulting in negligible leakage. Capsules/enzymes were a mixture of capsules, enzymes, buffer, and surfactant and resulted in measurable leakage within 15 hours. Enzyme alone produced fluorescence, but at a different spectral characteristic which can be discriminated from the fluorophore contained within the capsules.

FIG. 3 is a graph plotting rewetted fluorescence vs. exposure time of capsules/lipase/potassium phosphate/and surfactance immobilized onto Durx® 770 clean room wipes and maintained under dry (RH 40%) laboratory conditions (20-23° C.) following timed exposures to alpha particles from a 0.9 microCurie americium-241 source. The graph shows that alpha particle exposure enhances the enzymatic leakage of fluorescein dye from PLGA capsules. Capsules were exposed to alpha particle radiation from an Am-241 source for various lengths of time, and capsules were subsequently enzymatically degraded under dry (40% RH) laboratory conditions (20-23° C.). Amount of dye leakage was determined at 72 hours and correlates with the amount of alpha exposure experienced by the capsules.

FIG. 4 is a bar chart showing the fluorescence of intact (contained) and ruptured (released) PLGA microcapsules formulated with various internal fluorescent solutions including 4 mM sodium fluorescein, emulsified sodium fluorescein within mineral oil, 100 mM sodium fluorescein, and FAM-labelled peptide nucleic acid. In each case, the internal fluorescent solution is not indicated until the microcapsule is degraded by exposure to potassium hydroxide. This demonstrates that intact capsules effectively prevent visualization of fluorescence and that various fluorescent indicators can be used.

FIG. 5 is a bar chart showing the observed fluorescence of PLGA microcapsules filled with a sodium fluorescein solution after iterative exposure to various solvents. Four spots of microcapsules were deposited from a liquid suspension and dried on Durx® 770 clean room wipes and their fluorescence emission was determined (initial drydown). Each spot was then rewetted with ethanol and fluorescence remeasured (three times). Each spot was then rewetted with methanol and fluorescence remeasured (three times). Finally, each spot was degraded with potassium hydroxide which released the internal dye solution and caused marked increase in visual fluorescence.

DETAILED DESCRIPTION OF THE INVENTION

In a first aspect, the present disclosure is directed to a capsule composition containing at least or solely the following components: (a) a polyester shell, and (b) a solution containing a visual or olfactory indicator (i.e., indicator solution), wherein the indicator solution is encapsulated by the polyester shell. For purposes of the present invention, the polyester shell preferably has a thickness of no more than 20 microns, in order to ensure penetration of the alpha particle radiation through the entire shell thickness. Nevertheless, the polyester shell should be of sufficient thickness to retain the indicator solution prior to being etched by enzyme. In different embodiments, the polyester shell has a thickness of precisely, about, or less than, for example, 20, 18, 15, 12, 10, 8, 5, 2, 1 micron, or 50 nanometers, or a thickness within a range bounded by any two of the foregoing values (e.g., 50 nanometers-20 microns or 50 nanometers-18 microns, or 50 nanometers-15 microns).

The polyester shell is composed completely of or includes (e.g., as segments or in admixture) at least one polyester polymer containing ester (—C(O)O—) linkages at least in a backbone of the polyester polymer. The polyester polymer may or may not also have ester groups in pendant portions or terminal positions of the polymer. The polyester polymer can have any of a variety of possible number-average or weight-average molecular weights ($M_n$ or $M_w$, respectively). In different embodiments, the polyester polymer has a molecular weight of about, at least, greater than, up to, or less than, for example, 1,000 g/mol, 2,000 g/mol, 5,000 g/mol, 10,000 g/mol, 20,000 g/mol, 30,000 g/mol, 40,000 g/mol, 50,000 g/mol, 75,000 g/mol, 100,000 g/mol, 150,000 g/mol, 200,000 g/mol, 300,000 g/mol, 500,000 g/mol, or 1,000,000 g/mol, or a molecular weight within a range bounded by any two of the foregoing exemplary values.

In some embodiments, the polyester is a polyhydroxyalkanoate, which corresponds to the following generic structure:

(1)

In Formula (1), $R^1$ is selected from a hydrogen atom (H) or hydrocarbon group (R). The hydrocarbon group (R) can be any saturated or unsaturated hydrocarbon group, typically containing 1, 2, 3, 4, 5, 6, 7, 8, 9, 10, 11, or 12 carbon atoms or a number of carbon atoms within a range bounded by any two of the foregoing values (e.g., 1-12, 2-12, 3-12, 1-6, 1-4, or 1-3 carbon atoms). The hydrocarbon group (R) may be, for example, a straight-chained (linear) or branched alkyl or alkenyl group, or saturated or unsaturated cyclic hydrocarbon group. In some embodiments, the hydrocarbon group (R) is an alkyl group having one, two, three, four, five, or six carbon atoms, such as a methyl, ethyl, n-propyl, isopropyl, n-butyl, sec-butyl, n-pentyl, isopentyl, cyclopentyl, n-hexyl, isohexyl, or cyclohexyl group. The hydrocarbon group may, in some cases, be an unsaturated ring, such as a phenyl group. The hydrocarbon group may also be composed solely of carbon and hydrogen atoms, or may contain one or more heteroatoms selected from oxygen, nitrogen, and halogen atoms. Thus, in the case of cyclic hydrocarbon groups, the cyclic group may be a carbocyclic group or a heterocyclic group. The variable t is typically an integer from 0 to 4. The subscript t is more typically an integer from 0 to 3 (i.e., t is typically 0, 1, 2, or 3). The variable n is typically an integer of at least 10. In different embodiments, the subscript n is an integer of at least or greater than 10, 20, 50, 100, 200, 500, 1000, 1500, 2000, 2500, or 5000, or a value within a range bounded therein, or n can be a value that results in any of the exemplary molecular weights provided above. In some embodiments, any of the above classes or specific types of polyesters may be excluded from the polyester shell.

When t is 0, Formula (1) depicts a polymer of an alpha-hydroxy (α-hydroxy) acid. An example of an α-hydroxy polymer when $R^1$ in Formula (1) is H is polyglycolic acid. An example of an α-hydroxy polymer when $R^1$ is methyl is polylactic acid (i.e., PLA, polymer of 2-hydroxypropionic acid, also known as poly-L-lactic acid, poly-D-lactic acid, or poly-DL-lactic acid). An example of an α-hydroxy polymer when $R^1$ is phenyl is polymandelic acid. When t is 1, Formula (1) depicts a polymer of a beta-hydroxy (β-hydroxy) acid. An example of a β-hydroxy polymer when $R^1$ is H is poly(3-hydroxypropionic acid). An example of a β-hydroxy polymer when $R^1$ is methyl is poly(3-hydroxybutyric acid) (i.e., P3HB). An example of a β-hydroxy polymer when $R^1$ is ethyl is poly(3-hydroxyvaleric acid) (i.e., PHV). An example of a β-hydroxy polymer when $R^1$ is n-propyl is poly(3-hydroxyhexanoic acid) (i.e., PHH). When t is 2, Formula (1) depicts a polymer of a gamma-hydroxy (γ-hydroxy) acid. An example of a γ-hydroxy polymer when $R^1$ is H is poly(4-hydroxybutyric acid) (i.e., P4HB). An example of a γ-hydroxy polymer when $R^1$ is methyl is poly(4-hydroxyvaleric acid). Some examples of polyhydroxyalkanoates with t=3 include poly(5-hydroxyvaleric acid) and poly(5-hydroxyhexanoic acid). An example of a polyhydroxyalkanoate with t=4 includes poly (6-hydroxyhexanoic acid), also known as polycaprolactone (PCL). In some cases, the polyhydroxyalkanoate may be selected from poly(hydroxypropionic acid)s, poly(hydroxybutyric acid)s, poly(hydroxyvaleric acid)s, or poly(hydroxyhexanoic acid)s. The hydroxy acid need not be within the scope of Formula (1) to be suitable. For example, a polymer of salicylic acid may or may not also be considered. In some embodiments, any of the above classes or specific types of polyesters may be excluded from the polyester shell.

Copolymers of the hydroxy acids are also considered herein. In some embodiments, two or more different types of hydroxyalkanoates are in the copolymer, such as in (poly(lactic-co-glycolic acid) (i.e., PLGA), poly(3-hydroxybutyrate-co-3-hydroxyvalerate) (i.e., PHBV), or poly(3-hydroxybutyrate-co-3-hydroxyhexanoate). In other embodiments, the copolymer includes one or more non-hydroxyalkanoate portions, as in poly(glycolide-co-trimethylene carbonate) and poly(lactide-co-polyethylene glycol). In the case of a PLGA copolymer, the lactic acid (LA) and glycolic acid (GA) units in the PLGA copolymer may, in some embodiments, be independently present in a molar amount of 40-60%, wherein the molar amounts of lactic acid and glycolic acid units sum to 100%. The LA:GA molar ratio may be precisely or about, for example, 5:95, 10:90, 20:80, 30:70, 40:60, 45:55, 50:50, 55:45, or 60:40, or within a range between any two of the foregoing ratios. In some embodiments, any of the above classes or specific types of polyesters may be excluded from the polyester shell.

In some embodiments, the polyester is a diol-diacid type of polyester, i.e., a polyester resulting from the condensation of a diol with a diacid. The diol-diacid types of polyesters can be defined by the following generic structure:

(2)

In the above Formula (2), $R^2$ and $R^3$ are independently selected from hydrocarbon linking groups, which can be derived from hydrocarbon groups (R) containing 1-12 carbon atoms, as defined above, by replacing another hydrogen atom of the hydrocarbon group with a bond. For example, a methyl (—$CH_3$) group, selected from R groups, can have a hydrogen atom removed to result in a methylene (—$CH_2$—) linking group corresponding to $R^2$ and/or $R^3$. The variable n is as described above. In some embodiments, one or both (or at least one) of the linking groups $R^2$ and $R^3$ are independently selected from alkylene groups, i.e., linking groups of the formula —$(CH_2)_n$—, where m is typically 1-12. In other embodiments, one or both (or at least one) of the linking groups $R^2$ and $R^3$ are independently selected from saturated or unsaturated carbocyclic or heterocyclic groups (e.g., cyclopentyl, cyclohexyl, phenylene, and furan groups). In a first set of particular embodiments, $R^2$ is phenylene and $R^3$ is an alkylene group, in which case the polyester can be generally classified as a polyalkylene terephthalate. In the case where $R^2$ is phenylene and $R^3$ is methylene (—$CH_2$—), the polyester is a polymethylene terephthalate (PMT); in the case where $R^2$ is phenylene and $R^3$ is ethylene (—$CH_2CH_2$—), the polyester is a polyethylene terephthalate (PET); in the case where $R^2$ is phenylene and $R^3$ is propylene (—$CH_2CH_2CH_2$—), the polyester is a polypropylene terephthalate (PPT); in the case where $R^2$ is phenylene and $R^3$ is butylene (—$CH_2CH_2CH_2CH_2$—), the polyester is a polybutylene terephthalate (PBT). In a second set of particular embodiments, $R^2$ and $R^3$ are independently selected from alkylene groups. In the particular case where $R^2$ is ethylene, the polyester of Formula (2) is herein referred to as a succinate-based polyester, e.g., a polyethylene succinate, when $R^3$ is also ethylene; or a polypropylene succinate, when $R^3$ is propylene; or a polybutylene succinate, when $R^3$ is butylene. In the particular case where $R^2$ is butylene, the polyester of Formula (2) is herein referred to as an adipate-based polyester, e.g., a polyethylene adipate, when $R^3$ is ethylene; or a polypropylene adipate, when $R^3$ is propylene; or a polybutylene adipate, when $R^3$ is also butylene. In some embodiments, $R^2$ in Formula (2) may be a bond, which results in oxalate-based polyesters, such as polyethylene oxalates, when $R^3$ is ethylene. Other less common or more specialized polyesters according to Formula (2) are considered herein, such as when $R^2$ is naphthyl, which corresponds to the naphthalate-based polyesters, such as polyethylene naphthalate (PEN), when $R^3$ is ethylene, or polybutylene naphthalate (PBN), when $R^3$ is butylene. In some embodiments, any of the above classes or specific types of polyesters may be excluded from the polyester shell.

The polyester may alternatively be any of the vinyl ester and unsaturated polyester resins well known in the art. Vinyl ester resins are described, for example, in S. Jaswal et al., *Reviews in Chemical Engineering*, 30(6), 567-581 (2014); H. M. Kang et al., *Journal of Applied Polymer Science*, 79:1042-1053 (2001); and M. A. F. Robertson et al., *J. Adhesion*, 71:395-416 (1999), the contents of which are herein incorporated by reference in their entirety. Unsaturated polyester resins are described in, for example, H. Yang et al., *Applied Polymer*, 79(7), 1230-1242, 2001; M. Malik et al., *J. Macromol. Sci. Rev. Macromol. Chem. Phys.*, C40(2&3), 139-165 (2000); and M. Olesky et al., *Ind. Eng. Chem. Res.*, 52(20), 6713-6721 (2013), the contents of which are herein incorporated by reference in their entirety. In some embodiments, any of the above classes or specific types of polyesters may be excluded from the polyester shell.

The polyester can be terminated by any of the functional groups known in the art. In some embodiments, the polyester is acid-terminated (i.e., terminated with one or two carboxylic acid groups). In other embodiments, the polyester is ester-terminated (i.e., terminated with one or two carboxylic acid ester groups). In other embodiments, the polyester is hydroxy-terminated. In yet other embodiments, the polyester is amine-terminated or amide-terminated. The polyester may also have a combination of terminating groups, e.g., ester and hydroxy, or carboxylic acid and hydroxy.

The visual indicator can be any one or more substances that can be visually observed directly or indirectly when leaked from the capsule composition. Direct visualization is herein understood to mean visualization of the indicator with the eye of an observer, without an intermediary device to make the indicator visible. Indirect visualization is herein understood to mean visualization of the indicator by means of an intermediary device (e.g., a laser or wavelength detection or imaging device, or both) to make the indicator visible to the eye of the observer. Although in many embodiments the visual indicator is inherently visible the moment it becomes leaked, in some embodiments, the visual indicator may only become visible by reacting with another component after leaking, e.g., air or a second chemical contacted with a first leaked chemical.

In some embodiments, the visual indicator is a fluorophore. The fluorophore may absorb and emit light of any suitable wavelengths. In some embodiments, it may be desired to select a fluorophore with particular absorption and emission characteristics. For example, in different embodiments, the fluorophore absorbs at nanometer (nm) wavelengths of 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, or 800 nm, or a wavelength within a range bounded by any two of the foregoing values. In different embodiments, the fluorophore emits at any of the foregoing wavelengths, or within a range bounded by any two of the foregoing values, wherein it is understood that a fluorophore generally emits at a longer wavelength than the absorbed wavelength. The impinging electromagnetic radiation (i.e., which is absorbed by the fluorophore) can be in a dispersed form, or alternatively, in a focused form, such as a laser. Moreover, the absorbed or emitted radiation can be in the form of, for example, far infrared, infrared, far red, visible, near-ultraviolet, or ultraviolet.

In a first set of embodiments, the fluorophore is an organic molecule, which generally contains at least one carbon-carbon bond and at least one carbon-hydrogen bond. In different embodiments, the organic fluorophore can include, for example, a charged (i.e., ionic) molecule (e.g., sulfonate or ammonium groups), uncharged (i.e., neutral) molecule, saturated molecule, unsaturated molecule, cyclic molecule, bicyclic molecule, tricyclic molecule, polycyclic molecule, acyclic molecule, aromatic molecule, and/or heterocyclic molecule (i.e., by being ring-substituted by one or more heteroatoms selected from, for example, nitrogen, oxygen and sulfur). In the particular case of unsaturated fluorophores, the fluorophore may contain one, two, three, or more carbon-carbon and/or carbon-nitrogen double and/or triple bonds. In some embodiments, the fluorophore contains at least two (e.g., two, three, four, five, or more) conjugated double bonds (i.e., a polyene linker) aside from any aromatic group that may be in the fluorophore. In other embodiments, the fluorophore is a fused polycyclic aromatic hydrocarbon (PAH) containing at least two, three, four, five, or six rings (e.g., naphthalene, pyrene, anthracene, chrysene, triphenylene, tetracene, azulene, and phenanthrene) wherein the PAH can be optionally ring-substituted or derivatized by one, two, three or more heteroatoms. The fluorophore may be, for example, a xanthene derivative (e.g., fluorescein, rhodamine, Oregon green, eosin, or Texas Red), cyanine or its derivatives or subclasses (e.g., streptocyanines, hemicyanines, closed chain cyanines, phycocyanins, allophycocyanins, indocarbocyanines, oxacarbocyanines, thiacarbocyanines, merocyanins, and phthalocyanines), a naphthalene derivative (e.g., dansyl and prodan derivatives), a coumarin or derivative thereof, an oxadiazole or derivative thereof (e.g., pyridyloxazoles, nitrobenzoxadiazoles, and benzoxadiazoles), a pyrene or derivative thereof, an oxazine or derivative thereof (e.g., Nile Red, Nile Blue, and cresyl violet), an acridine (e.g., proflavin, acridine orange, and acridine yellow), an arylmethine (e.g., auramine, crystal violet, and malachite green), or tetrapyrrole (e.g., porphyrins and bilirubins).

In some embodiments, the fluorophore may be a cyanine dye (i.e., cyanine-based fluorophore). The term "cyanine dye", as used herein, refers to any of the dyes, known in the art, that include two indolyl or benzoxazole ring systems interconnected by a conjugated polyene linker. The cyanine dye typically contains at least two or three conjugated carbon-carbon double bonds, at least one of which is not in a ring, such as depicted in any of Formulas (1)-(3). The cyanine dye (or other type of dye) often contains at least two pyrrolyl rings. Some particular examples of cyanine dyes are the Cy® family of dyes, which include, for example, Cy2, Cy3, Cy3B, Cy3.5, Cy5, Cy5.5, Cy7, and Cy9. The term "cyanine moiety", as used herein, generally includes the bis-indolyl-polyene or bis-benzoxazolyl-polyene system, but excludes groups attached to the ring nitrogen atoms in the indolyl or benzoxazolyl groups. The cyanine dyes may also include the Alexa® family of dyes (e.g., Alexa Fluor 350, 405, 430, 488, 500, 514, 532, 546, 555, 568, 594, 610, 633, 647, 660, 680, 700, 750, and 790), the ATTO® family of dyes (e.g., ATTO 390, 425, 465, 488, 495, 520, 532, 550, 565, 590, 594, 601, 615, 619, 629, 635, 645, 663, 680, 700, 729, and 740), and the Dy® family of dyes (e.g., DY 530, 547, 548, 549, 550, 554, 556, 560, 590, 610, 615, 630, 631, 631, 632, 633, 634, 635, 636, 647, 648, 649, 650, 651, 652, 675, 676, 677, 680, 681, 682, 700, 701, 730, 731, 732, 734, 750, 751, 752, 776, 780, 781, 782, and 831). The ATTO dyes, in particular, can have several structural motifs, including, coumarin-based, rhodamine-based, carbopyronin-based, and oxazine-based structural motifs.

The fluorophore may alternatively be an inorganic fluorophore, such as a metal, metal oxide, or quantum dot nanoparticle or microparticle capable of fluorescing when stimulated. The fluorescing ability may be an innate property arising from the composition of the particle, or the fluorescing ability may arise from fluorophore doping or surface conjugation to an organic fluorophore species. The fluorescent dopant may be, for example, a lanthanide ion, such as, Ce, Er, Gd, Dy, or Yb. Some examples of metal particle fluorophores include gold and silver particles. Some examples of metal oxide fluorescent particles include fluorophore-doped silica, titania, or zirconia particles. Some examples of quantum dot nanoparticles include particles having a zinc sulfide, zinc selenide, zinc telluride, cadmium sulfide, cadmium selenide, or cadmium telluride composition. A detailed description of fluorescent nanoparticles is provided in S. M. Ng et al., *RSC Adv.*, 6, 21624-21661, 2016, which is herein incorporated by reference in its entirety.

In another embodiment, the visual indicator is a non-fluorophore dye. Some examples of non-fluorophore dyes include food colorants, azo dyes (e.g., Trypan Blue, Methyl Orange, FD&C Red 40, and FD&C Yellow 5), triphenylmethanes (e.g., Coomassie Blue and Bromocresol Green), Methylene Blue, Neutral Red, and Nile Blue. The term "non-fluorophore dye" herein refers to dyes that do not require electromagnetic stimulation to be visualized, i.e., the non-fluorophore dye has a color that can be visually observed directly with the eye. In some cases, the non-fluorophore dye may also possess a fluorescing property, which may be useful in further detecting the dye, in addition to being directly visually observable. Similarly, a fluorophore, such as any of the fluorophores described above, may also in some embodiments be directly visually observable, in addition to being indirectly observable by electromagnetic stimulation.

The olfactory indicator can be any compound or mixture of compounds that can be detected by humans, olfactory-acute animals, or electronic (i.e., artificial) olfactory sensing device. In embodiments where the olfactory indicator is intended to be detectable by a person, the olfactory indicator is selected to have a scent much stronger than required for detection by an olfactory-acute animal or electronic sensing device. The olfactory indicator may be or include, for example, an amine, thiol, ester (i.e., linear or lactone), ketone, terpene-containing compound, or aromatic compound. In some embodiments, the olfactory indicator may be a perfume (e.g., floral scent) or aromatic spice extract.

The visual or olfactory indicator is typically dissolved or suspended in a solvent, thereby resulting in a solution or suspension of the visual or olfactory indicator. The solvent can be any single solvent or mixture of solvents that suitably dissolve or suspend the visual or olfactory indicator while also not being in any way reactive with the polyester shell. The solvent may be or include, for example, aqueous-based (e.g., water or water admixed with a water-soluble co-solvent), alcohol (e.g., methanol, ethanol, n-propanol, iso-propanol, n-butanol, or ethylene glycol), nitrile (e.g., acetonitrile or propionitrile), or hydrocarbon (e.g., hexanes, paraffins, or mineral oil). Typically, a solvent that fully dissolves the visual or olfactory indicator is used. In some cases, the visual or olfactory indicator may itself be a liquid, in which case the visual or olfactory indicator may be encapsulated by the polyester shell by itself, i.e., not as a solution.

In another aspect, the present disclosure is directed to a method for preparing the capsule composition described above. Any liquid encapsulation method suited to producing capsules of liquid encapsulated by polyester shells may be used herein. The process may be, for example, an interfacial polymerization, in situ polymerization, coacervation, or emulsion process. In particular embodiments, the method includes a dual (double) emulsion process wherein an amount of a polyester, such as any of those described above, are dissolved in a solvent and homogenized with an indicator solution by ultrasound (e.g., an ultrasonic horn). The resultant emulsion may then be vortexed in one or more other solutions, followed by ultrasonic homogenization.

In another aspect, the present disclosure is directed to a method for detecting alpha particle radiation by use of the above-described capsule composition. In the method, an esterase is contacted with the capsule composition in a location of interest where presence of alpha particle radiation is being determined. The foregoing step of placing the capsule composition and esterase in a location of interest is herein referred to as "step (i)". The esterase functions as an initial etchant of the polyester shell to result in initial damage sites in the polyester shell, without causing leakage from the capsules. Alpha particle radiation, if present, will cause much quicker and more significant etching at the initial damage sites to the extent that leakage of the indicator solution will occur. Thus, alpha particle radiation can be determined to be present if leakage of the indicator solution from the capsules is observed to occur in a shorter time period than is known to occur from the esterase alone (i.e., in the absence of alpha particle radiation) over the same time period. The alpha emitting species may be any one or more radioactive elements, typically having an atomic number at or above 83, that emit alpha radiation, all of which are well known in the art. The alpha emitting species may be one or more alpha emitting isotopes of, for example, bismuth, polonium, radon, actinium, radium, americium, uranium, thorium, and plutonium.

The esterase can be any of the esterases known in the art, provided that the esterase is able to etch the polyester shell material. In particular embodiments, the esterase is a lipase. The esterase is typically contacted with the capsule composition in the further presence of a buffer and/or surfactant and/or a humectant. The buffer can be any of the pH buffering salts known in the art that can maintain a pH within which the esterase is active, of about 6-8, e.g., Tris buffer, HEPES buffer, or monobasic/dibasic phosphate buffer. The surfactant can be any of the amphiphilic molecules or polymers known in the art having lipophilic and hydrophilic portions, e.g., Triton™ X-100 or the polyoxyethylenesorbitans, such as polyethylene glycol sorbitan monolaurate (Tween® 20 or Polysorbate 20). The humectant may be any material which maintains some water activity around the enzyme and the microcapsule and may include for example polyvinylpyrrolidone, propylene glycol, glyceryl triacetate, honey, molasses, polydextrose, and sugar alcohols.

In a first set of embodiments, the method more particularly includes the following steps: (i) placing a capsule composition, as described above, and an esterase in contact with each other in a location where the presence of alpha particle radiation is being determined; (ii) waiting a period of time for the esterase to degrade the polyester shells, wherein the period of time is insufficient for the esterase to cause leakage of the solution from the capsule composition in the absence of alpha particle radiation, while the same period of time is sufficient for alpha particle radiation, if present, to degrade the polyester shells to the extent that leakage from the capsule composition would occur; and (iii) observing whether leakage from the capsule composition occurs at the completion of the period of time to determine whether alpha particle radiation is present. The period of time in which the esterase initially degrades the polyester shells without causing leakage of the capsules can be determined by a control experiment in which the esterase is contacted with the capsules in the absence of alpha particle radiation under the same conditions in which the testing of presence of alpha particle radiation is being conducted. The "same conditions" includes at least the same temperature, the same capsule and esterase compositions, same buffers and surfactants, and same ratio of esterase relative to capsule composition.

By the control experiment, the operator is aware of the period of time in which the esterase cannot cause leakage of the capsules on its own, i.e., in the absence of alpha particle radiation. In some embodiments, the esterase may, on its own, cause leakage of the capsules if present in sufficient amount and if given a sufficient period of time for the esterase to cause such degradation. Whether the esterase may, on its own, eventually cause leakage, can again be determined by a control experiment, and the operator is thus aware of the available period of time until the esterase can cause leakage on its own. In any event, to determine whether alpha particle radiation is present, the capsules in contact with esterase should be present in the location being tested for a period of time in which the esterase cannot cause leakage on its own. Thus, if leakage occurs at the completion of the period of time of the experiment, it can be deduced that alpha particle radiation is present. Moreover, in the event alpha particle radiation is determined to be present, the amount (magnitude) of alpha particle radiation may also be estimated by observation (which may include calculation) of the amount of leakage. To estimate the amount of alpha particle radiation, further controls can be conducted in which known levels of alpha particle radiation are tested on the capsules in contact with esterase to determine the levels of leakage resulting from the different levels of alpha particle radiation.

In other embodiments, the capsules (while in contact with the esterase) are placed in a location where the presence of alpha particle radiation is being determined for a period of time for the esterase to degrade the polyester shells to an extent that the solution within the capsules leaks out of at least a portion of the capsules. A subsequent step (step iii) involves detecting the leaked visual or olfactory indicator to determine the extent of leakage of the solution. A subsequent step (step iv) involves comparing the extent of leakage in step (iii) with the extent of leakage in a control experiment under the same conditions except that alpha particle radiation is known not to be present, wherein, if the extent of leakage observed in step (iii) is determined to be greater than the extent of leakage of the control, alpha particle radiation is determined to be present.

As discussed for any of the exemplary detection methods described above, an esterase is placed in contact with the capsule composition in a location where the presence of alpha particle radiation is being determined. The capsule composition can be contacted with the esterase by any suitable means. In one exemplary embodiment, the capsule composition and esterase are deposited on a surface in a location being tested by spraying droplets (e.g., a mist or fog) of both components onto the surface. In one embodiment, the two components are sprayed together (simultaneously). In another embodiment, the two components are sprayed separately (i.e., as separate sprays), which may be a simultaneous or successive spraying of the two sprays. In another exemplary embodiment, the capsule composition and esterase are first deposited on a sheet substrate material (e.g., paper, glass, ceramic, or metal) to produce a testing strip or sheet, and the testing strip or sheet is placed in a location where the presence of alpha particle radiation is being determined. The capsule composition and esterase can be deposited on the sheet substrate material by any suitable means (e.g., spray coating or dipping followed by drying), provided that the means for doing so does not interfere with the ability of the capsules to be etched by the esterase and alpha particle radiation.

In some embodiments, to more precisely determine whether leakage is a result of the presence of an alpha radiation emitter, an alpha radiation blocking layer is positioned over a portion of the capsule composition and esterase when the capsule composition and esterase are placed in a location where the presence of alpha particle radiation is being determined. The operator should then compare the presence or extent of leakage of the indicator solution from capsules in regions covered by the alpha radiation blocking layer and regions not covered by the alpha radiation blocking layer to determine if regions not covered by the alpha radiation blocking layer exhibit leakage or a higher leakage of the solution compared to regions covered by the alpha radiation blocking layer. If no (or less) leakage is observed in the capsule composition covered by the alpha radiation blocking layer compared to the capsule composition not covered by the alpha radiation blocking layer, the operator has further evidence that alpha radiation is present. The alpha radiation blocking material can be any material well known in the art having a propensity for at least partially blocking alpha particle radiation, e.g., a sheet, strip, or other shape of paper, plastic, or metallic foil.

The visual or olfactory indicator, once leaked, can be observed by any suitable means. In the case of a fluorophore visual indicator, the fluorophore is typically stimulated with electromagnetic radiation (e.g., by laser light) to result in emission of light that can be observed directly by the eye or through glasses or other device having a wavelength filter. In the case of an olfactory indicator, the leaked scent may be observed directly by a human operator, or indirectly by use of an olfactory-acute animal (e.g., sniff dog) or artificial olfactory device.

In some embodiments, the detection method described above is specifically directed to the detection of radon. The presence of radon may be determined by any of the methods described above. However, as radon shares the unusual characteristic of being a gaseous alpha radiation emitter, the above described methods can be more specifically tailored for radon testing. In one set of embodiments, the method for radon testing includes, before step (i), placing an absorbent material that absorbs radon yet does not block alpha particle emission in a location where the presence of radon is being determined. The absorbent material can be, for example, a cryptophane material or a modified or related form thereof, wherein cryptophanes and derivatives thereof are known in the art to be particularly adept in absorbing radon (e.g., D. R. Jacobson et al., Proc Natl Acad Sci USA. 2011 Jul. 5; 108(27): 10969-10973; L. Laureano-Perez et al., Applied Radiation and Isotopes, 70(9), pp. 1997-2001, September 2012; and K. T. Holman, "Cryptophanes: Molecular Containers", in Atwood, J. L.; Steed, J. W. (eds.). Encyclopedia of Supramolecular Chemistry. CRC Press, 2004. pp. 340-348. doi:10.1081/E-ESMC. ISBN 0-8247-4723-2). In some embodiments, the cryptophane is more specifically Cryptophane A. Other radon absorbants include bisphenol-A based polycarbonates, activated charcoal, and various oils including olive oil, and other vegetable oils. After the absorbent material is provided sufficient time to absorb radon (e.g., at least 1, 2, 3, or 4 days), the capsule composition and esterase are placed in contact with each other on the absorbent material in accordance with step (i). Subsequently, the capsule composition is monitored for leakage over a period of time, as discussed above, in accordance with steps (ii) and (iii), to determine the presence of radon.

In further embodiments of the above radon detection method, the method may further involve, before step (i), placing the radon-absorbing (absorbent) material on selective portions of a substrate to result in regions of the substrate containing (coated with) the absorbent material and regions of the substrate not containing (not coated with) the absorbent material. The substrate, whose surface is selectively coated with the absorbent material, is then placed in a location where the presence of radon is being determined. After the absorbent material is provided sufficient time to absorb radon, the capsule composition and esterase are placed in contact with each other on regions containing the absorbent material and regions not containing the absorbent material, in accordance with step (i). Subsequently, the capsule composition is monitored for leakage over a period of time, as discussed above, in accordance with steps (ii) and (iii), to determine the presence of radon. In the foregoing embodiment, step (iii) more particularly includes determining the presence or extent of leakage of the solution in regions containing the absorbent material and comparing this result to regions not containing the absorbent material to determine if regions containing the absorbent material exhibit leakage (or a higher leakage) of the indicator solution from the capsules compared to regions not containing the absorbent material.

Examples have been set forth below for the purpose of illustration and to describe certain specific embodiments of the invention. However, the scope of this invention is not to be in any way limited by the examples set forth herein.

Examples

Method and Apparatus for Determining the Location of Alpha Particle-Generating Radioactive Contamination Disclosed is a method and apparatus for determining the location of alpha particle-generating radioactive contamination. Track etch recording polymeric micro- and/or nanocapsules are filled with an indicator material and co-deposited with materials which etch or degrade the polymeric shell and for which this etching and degradation is dependent and/or sensitized and enhanced by the damage tracks imparted to the polymer by exposure to alpha particle radiation. Capsule degradation by the combined influence of the etchant and alpha-particle radiation results in leakage of the capsule contents which may be measured by various methods to quantitatively determine the precise location of alpha-emitting radioactive contaminants upon surfaces upon which the etchant and nanocapsules have been colocalized.

A preferred embodiment of the capsules are fluorescent dye-containing nanocapsules produced via a dual emulsion technique whereby 25 milligrams of poly(lactic-co-glycolic) acid (PLGA) are dissolved in 1 milliliter of ethyl acetate and homogenized with an ultrasonic horn with 50 microliters of 10 mM sodium fluorescein in water. The resultant emulsion is then vortexed into 2 milliliters of a solution of 0.3% D-alpha-tocopherol polyethylene glycol in water, followed by ultrasonic homogenization. This emulsion is then vortexed into 50 mL of the 0.3% E-TPGS solution, resulting in hardening of the PLGA capsules and formation of core shell particles of sodium fluorescein within PLGA.

Figure 1:
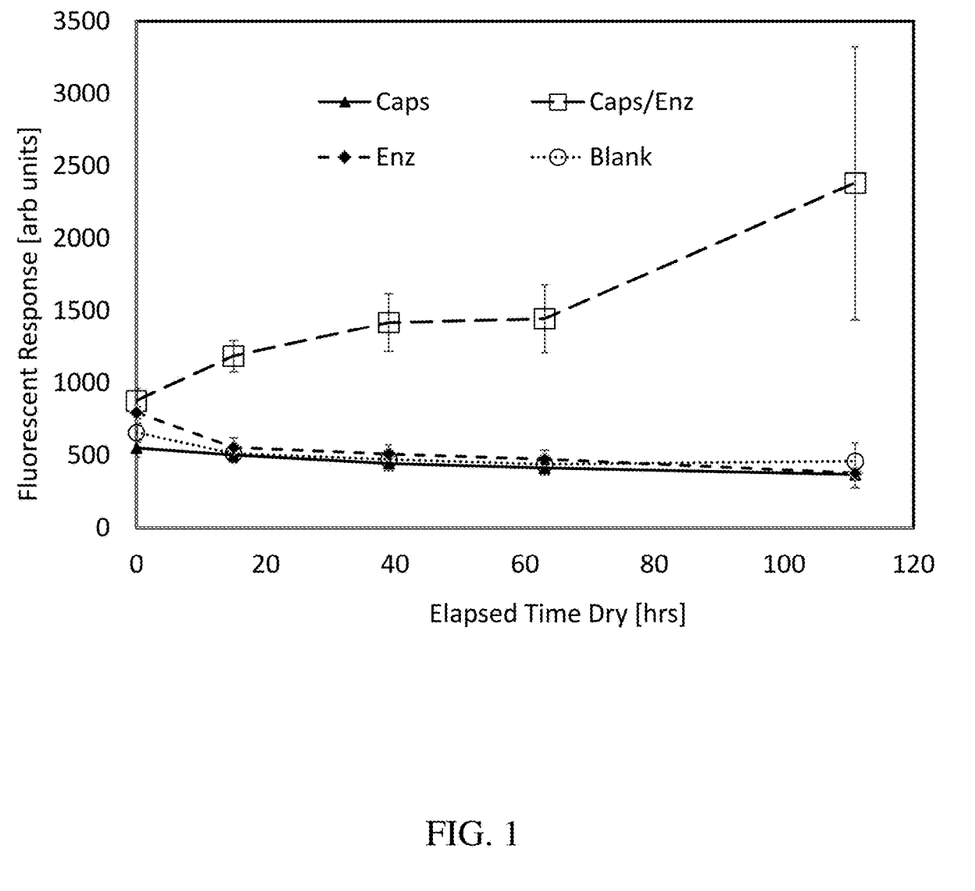

Polymeric capsules are colocalized with an etchant and factors promoting the degradation of the nanocapsules by the etchant. A preferred embodiment is to colocalize the polymeric capsules with lipase derived from *Rhizopus oryzae*, pH buffer salts, and the surfactant Tween® 20 which slowly degrades the polymeric capsules over time even under dry conditions. This degradation is significantly enhanced by exposure of the polymeric capsules to alpha particle radiation. FIG. 1 is a graph showing the amount of leakage of fluorescein dye from PLGA nanocapsules deposited onto Durx® 770 polyester/cellulose clean room wipes and exposed to lipase over extended periods of time.

A preferred embodiment for colocalization of the polymeric capsules and the etchants is aerosol dispersal of these materials using, for example, an aerosol fogging approach similar to insect 'bombs' used for dispersal of insecticides within interior enclosures. Polymeric capsules and etchant materials are initially stored in separate compartments and mixed upon activation of the aerosol dispersal device, generating an aerosol fog in which individual aerosol particles contain both the polymeric capsules and the etchant mix, thereby allowing these materials to colocalize upon surfaces within the fogged enclosure.

Colocalization of the polymeric capsules and etchant materials may also be performed by spraying the individual or mixed components upon surfaces including walls, floors, tabletops, and upon materials that may be wiped upon these surfaces such as cloths, sampling swabs, and upon other materials such as clothing, shoe soles, carpets, floor coverings, enclosure housings such as tents. Colocalization may also be achieved by containing both the indicator dye and the etchant mixture (for example, enzyme, buffer, and surfactant) within the capsules, provided there is a significant difference in the etch rate of the polymer with and without alpha radiation exposure.

Polymeric capsule degradation, facilitated by alpha particle exposure, may be quantified and localized via various methods. A preferred embodiment is to contain a fluorescent dye within the capsule and to observe leakage of the dye due to capsule degradation via fluorescent imaging systems which may include laser illuminators and appropriately filtered laser safety goggles, illuminators and cameras with appropriate wavelength filtering. Dyes may also be non-fluorescent and colorimetric for ambient light visualization or reactive for detection using an indicator reagent. Capsules may also contain other materials that may be detected by other measurement modalities, including scents to which canines are trained or other odorants. A preferred embodiment is to fill capsules with sodium fluorescein and to observe capsule degradation via use of a 520 nm laser diode flashlight, and Thorlabs LG3 laser safety goggles with 545 nm high pass emission filtering.

Figure 2:
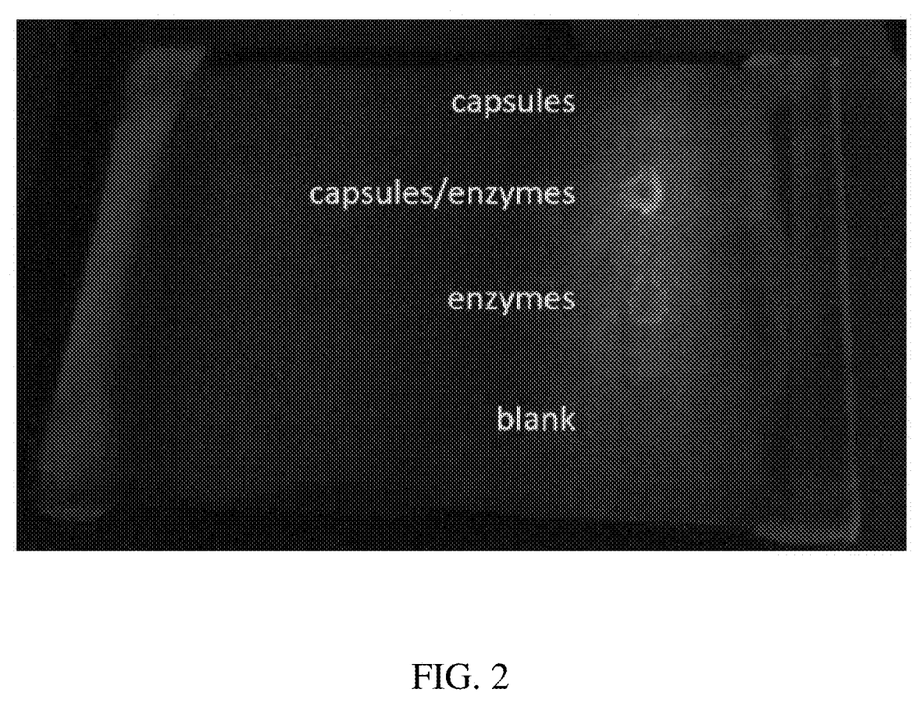

FIG. 2 presents an optical image of a clean room wipe (Durx® 770) which has been pretreated with nanocapsules containing fluorescein and *Rhizopus oryzae* lipase with phosphate buffer salts and Tween® 20, which has degraded the capsules over time while the wipe was maintained in a dry, laboratory environment. The materials were deposited upon the wipe as 2 microliter spots as capsules alone, capsules with degradative enzyme, enzyme alone, and blanks (no capsules nor enzymes). The capsule/enzyme combination resulted in degradation of the capsules and leakage of the internal fluorescein dye, visualized by 520 nm laser diode excitation and filtering with LG3 laser safety goggles.

Figure 3:
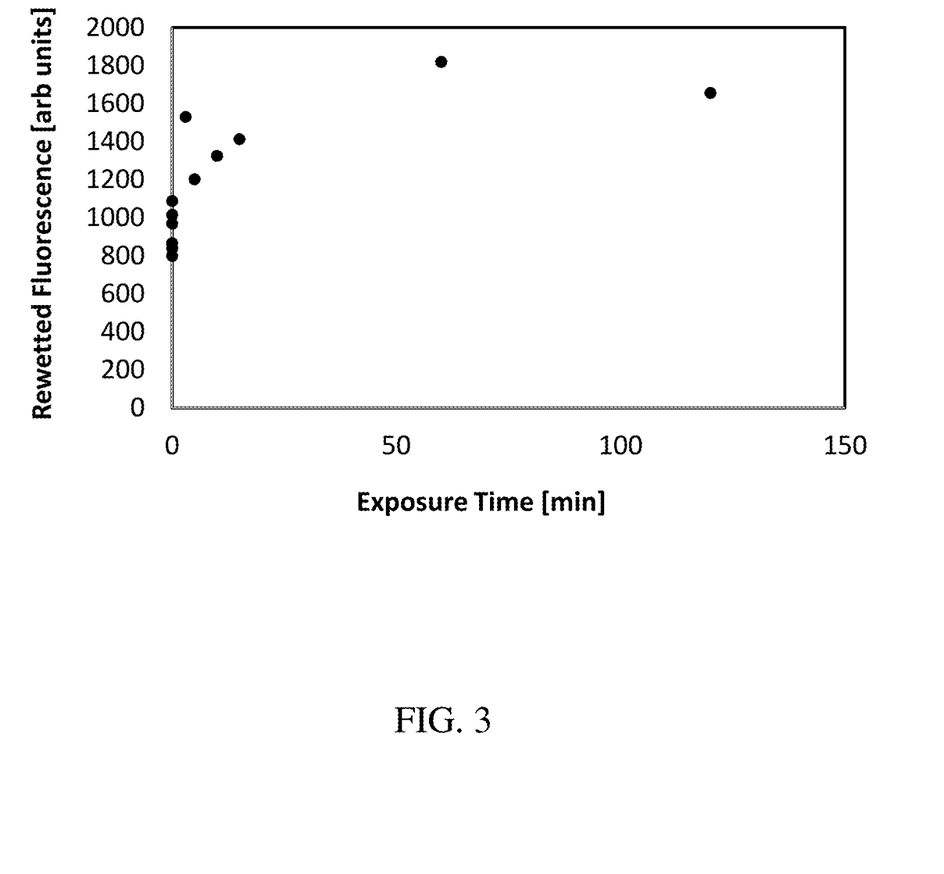
Figure 4:
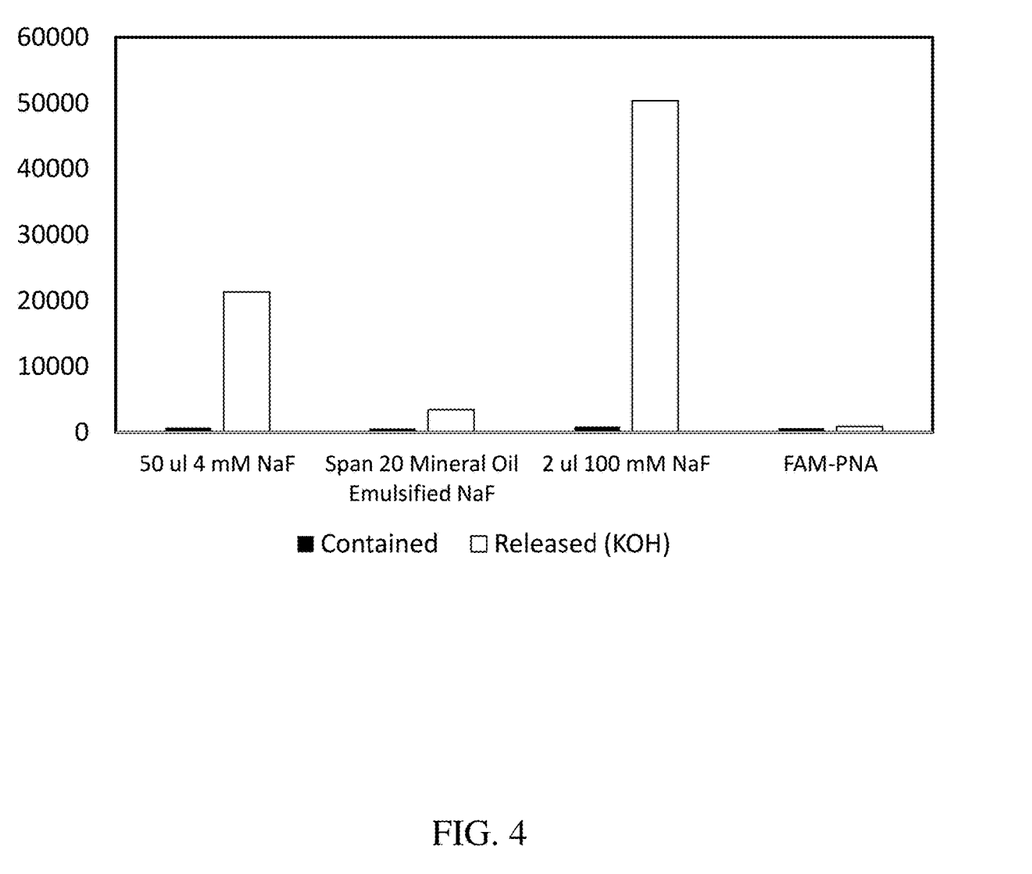
Figure 5:
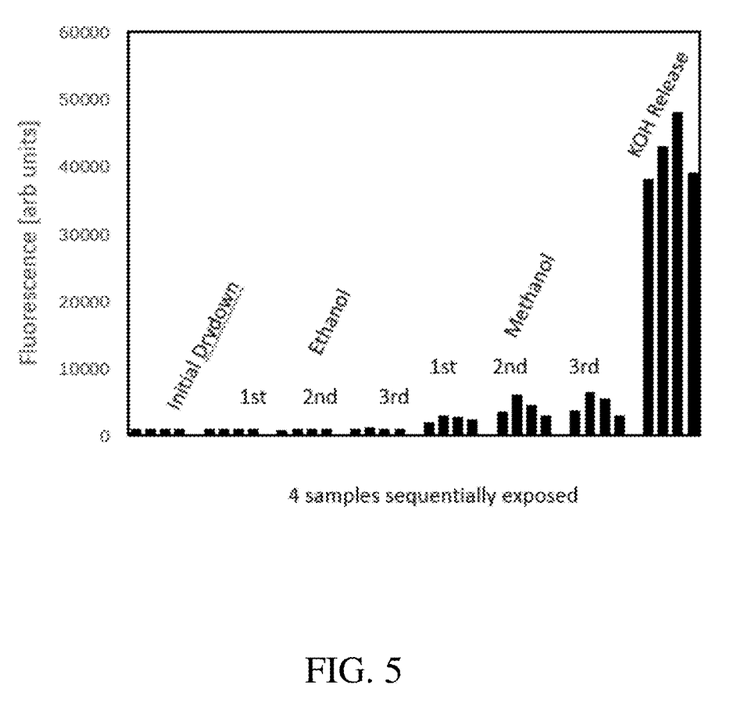
Figure 6:
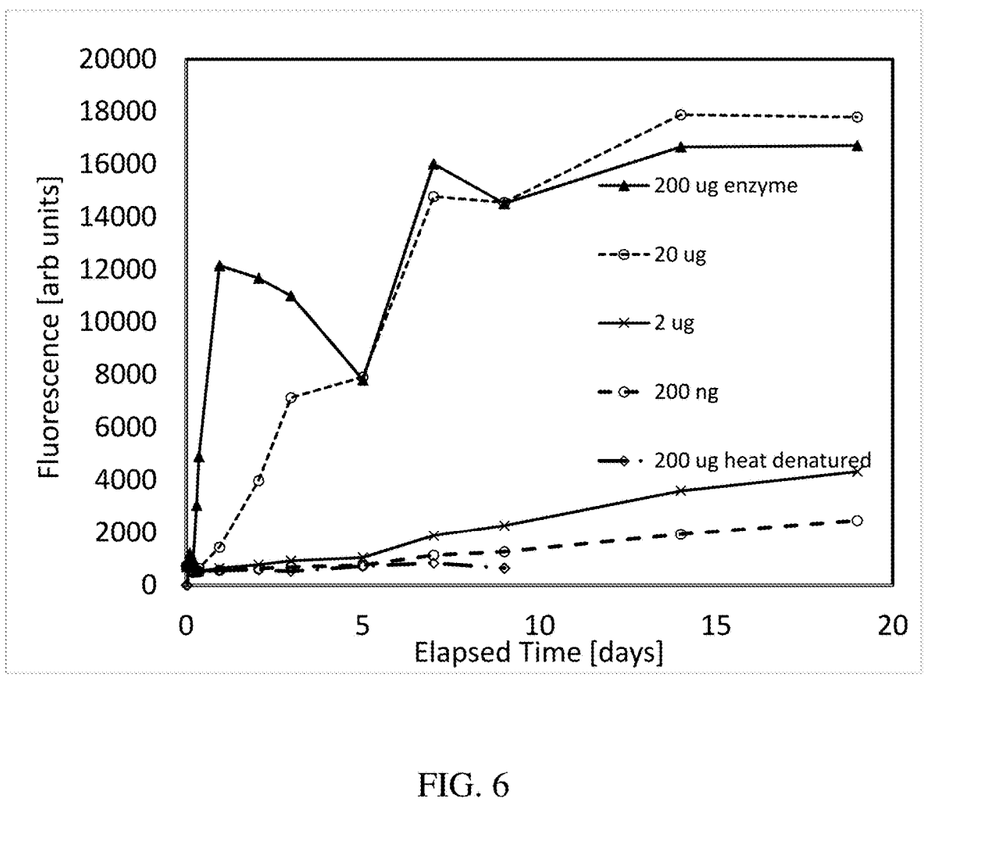
FIG. 6 is a line chart of the fluorescence emission from PLGA microcapsules containing sodium fluorescein over time when colocalized with potassium phosphate buffer (pH 8.0) triton x-100 and various amounts of lipase enzyme. Increasing the amount of lipase results in faster degradation and fluorescence release from microcapsules. Heat denaturation of the enzyme diminishes the enzymes ability to degrade and release fluorescence from the microcapsules.

A preferred embodiment is to simultaneously disperse a variety of capsules filled with fluorophores with unique and separate excitation/emission characteristics such that capsule degradation will be observable at multiple wavelengths and thereby easy to discriminate against other fluorescent materials within the search vicinity. The degradation of polymeric capsules is dependent upon alpha-particle exposure and is specifically dependent upon alpha particles impinging upon and traveling through the polymeric shell and inducing a damage track through the material which subsequently enables or enhances the degradation of that material along that damage track by the etchant. A classic example is alpha track etch recording whereby alpha particle tracks within polycarbonate may be etched by a strong base. Similarly, the preferred embodiment of PLGA may be sensitized to enzymatic etching by exposure of the PLGA capsules to alpha particle radiation. Other polymeric materials may also be used, and various polymer/enzyme combinations employed. FIG. 3 presents the amount of fluorescein leaked from PLGA nanocapsules co-immobilized onto Durx® clean room wipes with lipase enzyme and following exposure of those capsules to various doses of alpha particle radiation from an Am-241 source. The alpha particle exposure sensitized the PLGA nanocapsules to degradation and facilitated leakage of fluorescein from the capsules.

The system is useful for determining the precise location of alpha-particle emitting radioactive contamination. Isotopic alpha particles travel several centimeters in air and are stopped by materials based upon the interactions of the alpha particle and the material. As such, deposition of the capsule/etchant materials upon surfaces will accurately reveal alpha contamination within several centimeters and the amount of indicator released from the system will be dose dependent.

The system is useful for alpha-particle emitting contaminant including but not limited to the following principle radioactive materials: 209Bi, 211Bi, 212Bi, 213Bi, 210Po, 211Po, 212Po, 214Po, 215Po, 216Po, 218Po, 215At, 217At, 218At, 218Rn, 219Rn, 220Rn, 222Rn, 226Rn, 221Fr, 223Ra, 224Ra, 226Ra, 225Ac, 227Ac, 227Th, 228Th, 229Th, 230Th, 232Th, 231 Pa, 233U, 234U, 235U, 236U, 238U, 237Np, 238Pu, 239Pu, 240Pu, 244Pu, 241Am, 244Cm, 245Cm, 248Cm, 249Cf, and 252Cf.

A preferred embodiment to implement the above-described system is to deploy an aerosol bomb in a room in which alpha contamination is suspected and to close access to the room for 12 or more hours. Following this interval, the room is inspected by scanning the room with a laser flashlight and appropriately filtered laser safety glasses, or by implementing a LIDAR device to spatially map the room and denote areas where the unique fluorescent signatures of the capsule system are indicated. This will permit decontamination crews to plan their decontamination operations to safety and effectively remove or seal the precise sources of alpha emitting radioactive contaminants.

Another preferred embodiment is to co-localize dye containing capsules and etchant materials onto solid materials (such as fabrics and coverings) and to lay these materials upon a surface for extended periods of time such that alpha emitting contaminants upon that surface will irradiate the overlaying capsule-bearing cover. This approach eliminates the need for aerosol dispersal and may be preferred in some scenarios.

Another preferred embodiment is for radon detection. Small strips of paper are surface treated with nanocapsules containing a colorimetric dry and an appropriate chemical or enzymatic etchant, as described above. These detectors are then placed in areas to monitor for the presence of alpha emitting radon gas within the environment over extended time periods (i.e. months). Preferred areas are low-lying areas with minimal air exchange where dense radon gas might collect. Radon exposure will result in alpha irradiation of the capsules, thereby promoting their rupture and release of dye over extended time periods. As a positive control, a pre-irradiated region on the test strip (pre-irradiated with a known dose of alpha radiation) can be used as an indicator that the colorimetric test strip remains functional.

Such test strips can be inexpensively manufactured by spotting or printing the capsules onto small regions of paper, and to use an adhesive backing on the paper (similar to post-it notes) to affix the indicators to surfaces of interest. The indicators can be read on a periodic basis by looking for the colorimetric indication of capsule rupture which is dependent upon alpha exposure. Such indicators could be combined with other radon gas measurement modalities (such as charcoal traps, which must be laboratory analyzed after a specific collection period has elapsed), or ionization chambers which are expensive single point analysis systems.

PLGA Capsule Production

PLGA capsules were produced using a double emulsion method. 25 mg of PLGA (Resomer RG503:comprised of acid-terminated, lactide:glycolide 50:50, MW 24000-38000) or (Lactel B6010-2:comprised of ester terminated, lactide: glycolide 50:50, MW 30000-60000) was dissolved in 1 mL of ethyl acetate in a 13 mm×100 mm glass test tube. 2 microliters of 100 mM sodium fluorescein (dissolved in water) was added to the dissolved polymer solution and placed onto wet ice while homogenized for 10 seconds with a 700 W ultrasonic homogenizer set at 40% amplitude. The resultant emulsion was then added dropwise using a glass Pasteur pipette to 2 mL of 0.3% tocopherol polyethylene glycol succinate (in water) while vortexing the solution within a 13 mm×100 mm glass test tube on a laboratory vortexer. The resultant emulsion was then placed on ice and ultrasonicated for 3 cycles of 10-secs/10-sec rest. The resultant emulsion was then decanted into 45 mL of 0.3% weight/volume tocopherol polyethylene glycol succinate stirred at 360 rpm. The mixture was stirred overnight to allow hardening of the PLGA capsules via loss of ethyl acetate from the polymer emulsion into the aqueous solution. Other variations of capsules were produced by altering the volume or concentration of sodium fluorescein added to the PLGA-ethyl acetate solution, or by using other fluorophores or other additives to the encapsulated solutions such as mineral oil and surfactants.

PLGA capsules were collected by centrifuging the mixture for 15 minutes at 17000 g in a fixed-angle ultracentrifuge. The supernatant was decanted and the capsules were re-suspended in 50 mL of water chilled to 4° C. This procedure was repeated twice to result in PLGA capsules suspended in water, with the final volume of added water being 4 mL. PLGA capsules in aqueous suspension were stored at 4° C.

Total Dye Loading of PLGA Capsules

Total dye loading of capsules was determined by saponification. PLGA capsules were re-suspended into 10 mM potassium phosphate buffer (pH 8.0) with 0.05% Tween® 20 or 1M potassium hydroxide by microcentrifuging 100 μL of the capsules at 10000 g for 2 minutes, aspirating the supernatant, and re-suspending the capsules in 100 μL of the respective solution. Fluorescence of the solution was assayed on a Perkin Elmer HTS 7000 plate reader using a filter set for fluorescein (485 nm excitation/520 nm emission) and a gain of 55. FIG. 4 summarizes the fluorescence emission of variously formulated capsules that continue to contain their encapsulated dye (by suspension within potassium phosphate buffer and Tween) vs. those that released their dye due to saponification with potassium hydroxide.

Immobilization of PLGA Capsules on Surfaces

PLGA capsules were re-suspended into 10 mM potassium phosphate buffer (pH 8.0) with 0.05% Tween® 20 by microcentrifuging 100 μL of the capsules at 10000 g for 2 minutes, aspirating the supernatant, and re-suspending the capsules in 100 μL of the buffer/surfactant solution. A modified 96-well plate was prepared by removing the plate bottom and affixing a sheet of Durx® 770 clean room wipe to the plate to serve as a plate bottom. Capsule suspension was dispensed in 1-2 microliter volumes onto the Durx® 770 clean room wipes at fixed well locations, and allowed to dry.

Evaluation of Stability of PLGA Capsules to Solvent Exposure

The fixed well locations were subsequently and iteratively rewetted with ethanol, methanol, and potassium hydroxide to evaluate the stability of the capsule to ethanol and methanol solvents. Fluorescence of the capsules at fixed well locations were assayed on a Perkin Elmer HTS 7000 plate reader using a filter set for fluorescein (485 nm excitation/520 nm emission). FIG. 5 summarizes the fluorescence emission of PLGA capsules after initial drying, after iterative wetting with ethanol and methanol, and after saponification and dye release by exposure to 1M potassium hydroxide.

Evaluation of Enzymatic Degradation of Capsules 50 microliters of PLGA capsules were re-suspended into 10 mM potassium phosphate buffer (pH 8.0) with 0.05% Tween® 20 and 2 μL was spotted into each of 24 microwells on a plate. Lipase derived from *Rhizopus oryzae* was formulated at 1 mg in 10 μL of 10 mM potassium phosphate (pH 8.0) with 0.05% Tween® 20. 2 μL of this was added to spots on 2 wells, then diluted 1:10 and this added to capsule spots in two wells, serially down to 20 ng per reaction. Each of the enzyme dilutions was also placed in hot (90° C.+) water for 10 minutes and this was also spotted to co-localize with PLGA capsules.

Fluorescence of the capsules at fixed well locations were assayed on a Perkin Elmer HTS 7000 plate reader after a period of 19 days using a filter set for fluorescein (485 nm excitation/520 nm emission). Periodically, the spots were rewetted briefly (minutes) to promote leakage of the dry fluorescein within the capsules. The results are provided in FIG. 6. Increasing enzyme concentration resulted in higher amounts of fluorescence due to dye leakage. Heat denatured enzyme, even at the highest concentrations of enzyme used, resulted in substantially less fluorescence due to leakage.

Evaluation of Alpha-Induced Enzymatic Degradation of Capsules

PLGA capsules were re-suspended into 10 mM potassium phosphate buffer (pH 8.0) with 0.05% Tween® 20 and 50 micrograms of lipase from *Rhizopus oryzae*. 2 μL aliquots were spotted into individual wells of a 96-well plate with the bottom removed and replaced by a sheet of Durx® 770 clean room wipe. Spots were allowed to dry and irradiated for various times (120 min, 60 min, 15 min, 10 min, 5 min, 2 min) with a 0.9 microcurie Americium-241 alpha source where the alpha source was located 1 cm above each spot. The spots were rewetted with 2 microliters of water at 72 hrs and the fluorescence was measured using a Perkin Elmer HTS 7000 plate reader with fluorescein filter set. Alpha exposure resulted in increased fluorescence from the capsule spots (n=6 samples) vs. capsules that were not irradiated (n=6) due to enhanced degradation of the capsule, as shown in FIG. 3.

Improved Sensitivity to Alpha-Induced Degradation of Capsules

Figure 7A:
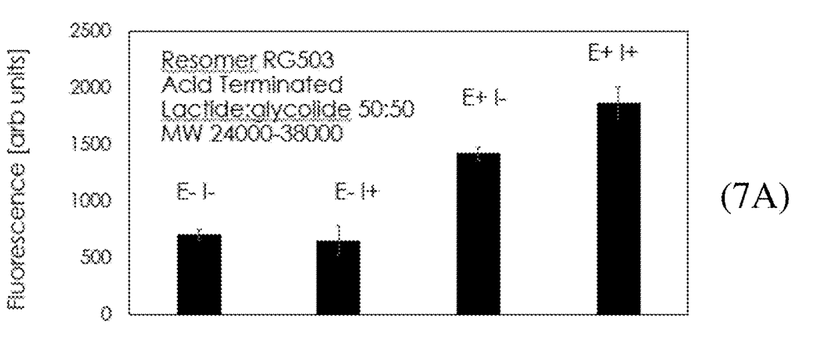
FIGS. 7A and 7B are bar charts which demonstrate that different formulations of PLGA result in differing characteristics with respect to enzymatic etching and the impact of alpha particle exposure prior to etching. Microcapsules containing sodium fluorescein were co-localized with (E+) and without (E−) enzyme, and with (I+) and without (I−) 2 minutes of alpha particle exposure 1 cm from a 0.9 micro-Curie Am-241 source. Resomer RG503 microcapsules (FIG. 7A) have some level of leakage without enzyme exposure. Enzyme exposure increases the leakage and irradiation further increases this leakage. Lactel B6010 microcapsules (FIG. 7B) provide a larger difference when irradiated, whereby the irradiation appears to enhance enzymatic degradation of the microcapsule.
Figure 7B:
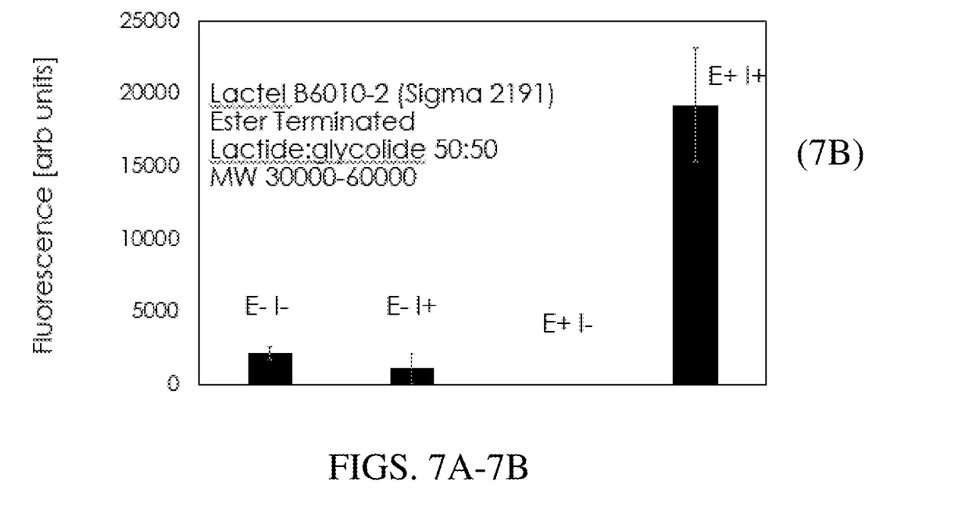

PLGA capsules produced using either Resomer RG503 or Lactel B6010-2 PLGA were re-suspended into 10 mM potassium phosphate buffer (pH 8.0) with 0.05% Tween® 20 with and without 1/20 Unit of lipase from *Rhizopus oryzae*. 2 μL aliquots of each PLGA type (Resomer or Lactel) were spotted into 12 individual wells of a 96-well plate (6 with enzyme, E+ and 6 without enzyme E−) with the bottom removed and replaced by a sheet of Durx® 770 clean room wipe. Spots were allowed to dry and half of each PLGA type was irradiated for 2 minutes with a 0.9 microcurie Americium-241 alpha source where the alpha source was located 1 cm above each spot (E−I+=no enzyme irradiated; E+I+ =enzyme and irradiated). The spots were rewetted with 2 microliters of water at 72 hrs and the fluorescence was measured using a Perkin Elmer HTS 7000 plate reader with fluorescein filter set. As shown in FIGS. 7A and 7B, while the Resomer microcapsules (FIG. 7A) resulted in significant fluorescence due to enzyme etching alone, the Lactel PLGA capsules (FIG. 7B) presented a larger irradiation induced leakage compared to unirradiated enzymatic degradation of the capsules compared against the Resomer PLGA formulation. This permits greater sensitivity to alpha particle radiation and may increase the length of time that microcapsule and enzymes can be colocalized before resulting in leakage due to enzyme activity alone without alpha exposure.

While there have been shown and described what are at present considered the preferred embodiments of the invention, those skilled in the art may make various changes and modifications which remain within the scope of the invention defined by the appended claims.

What is claimed is:

1. A capsule composition comprising: (a) a polyester shell having a thickness of no more than 20 microns, and (b) a solution containing a visual indicator, wherein said solution is encapsulated by said polyester shell; wherein said polyester is ester-terminated and has a number-average or weight-average molecular weight of at least 20,000 g/mol.

2. The capsule composition of claim 1, wherein said polyester is a polyhydroxyalkanoate having the following structure:

wherein $R^1$ is selected from a hydrogen atom or hydrocarbon group, t is an integer from 0 to 4, n is an integer of at least 10, and said structure can be a homopolymer or copolymer.

3. The capsule composition of claim 2, wherein said polyhydroxyalkanoate is selected from the group consisting of polylactic acid, polyglycolic acid, poly(3-hydroxypropionic acid), poly(hydroxybutyric acid)s, poly(hydroxyvaleric acid)s, poly(hydroxyhexanoic acid)s, polycaprolactone, polymandelic acid, and copolymers thereof.

4. The capsule composition of claim 2, wherein said polyhydroxyalkanoate comprises polylactic acid, polyglycolic acid, or copolymer thereof.

5. The capsule composition of claim 2, wherein said polyhydroxyalkanoate comprises a copolymer of lactic acid and glycolic acid.

6. The capsule composition of claim 5, wherein said lactic acid and glycolic acid units in said copolymer are independently present in a molar amount of 40-60%, wherein the molar amounts of lactic acid and glycolic acid units sum to 100%.

7. The capsule composition of claim 1, wherein said polyester has a number-average or weight-average molecular weight of at least 30,000 g/mol.

8. The capsule composition of claim 1, wherein said polyester has a number-average or weight-average molecular weight of at least 40,000 g/mol.

9. The capsule composition of claim 1, wherein said polyester is acid-terminated.

10. The capsule composition of claim 1, wherein said visual indicator is a fluorophore.

11. The capsule composition of claim 1, wherein said visual indicator is a non-fluorophore dye.

12. A method for detecting alpha particle radiation, the method comprising:
(i) placing a capsule composition and esterase in contact with each other in a location where the presence of alpha particle radiation is being determined, wherein said capsule composition comprises: (a) polyester shells having a thickness of no more than 20 microns, and (b) a solution containing a visual or olfactory indicator, wherein said solution is encapsulated by said polyester shells;
(ii) waiting a period of time for the esterase to degrade the polyester shells, wherein said period of time is insufficient for the esterase to cause leakage of the solution from the capsule composition in the absence of alpha particle radiation, while said period of time is sufficient for alpha particle radiation, if present, to degrade the polyester shells to the extent that leakage from the capsule composition would occur; and
(iii) observing whether leakage from the capsule composition occurs at the completion of said period of time to determine whether alpha particle radiation is present.

13. The method of claim 12, wherein, in step (iii), if alpha particle radiation is determined to be present, the magnitude of alpha particle radiation is also determined by observing the degree of capsule leakage.

14. The method of claim 13, wherein said polyester is a polyhydroxyalkanoate having the following structure:

wherein R¹ is selected from a hydrogen atom or hydrocarbon group, t is an integer from 0 to 4, n is an integer of at least 10, and said structure can be a homopolymer or copolymer.

15. The method of claim 14, wherein said polyhydroxyalkanoate is selected from the group consisting of polylactic acid, polyglycolic acid, poly(3-hydroxypropionic acid), poly(hydroxybutyric acid)s, poly(hydroxyvaleric acid)s, poly(hydroxyhexanoic acid)s, polycaprolactone, polymandelic acid, and copolymers thereof.

16. The method of claim 14, wherein said polyhydroxyalkanoate comprises polylactic acid, polyglycolic acid, or copolymer thereof.

17. The method of claim 14, wherein said polyhydroxyalkanoate comprises a copolymer of lactic acid and glycolic acid.

18. The method of claim 12, wherein said esterase is a lipase.

19. The method of claim 12, wherein the alpha emitting particles comprise radon.

20. The method of claim 19, wherein, before step (i), the method further comprises placing an absorbent material that absorbs radon yet does not block alpha particle emission in a location where the presence of radon is being determined, and, in step (i), placing the capsule composition and esterase in contact with each other on said absorbent material after the absorbent material is provided sufficient time to absorb radon.

21. The method of claim 19, wherein, before step (i), the method further comprises placing an absorbent material that absorbs radon yet does not block alpha particle emission on selective portions of a substrate to result in regions of the substrate containing the absorbent material and regions of the substrate not containing the absorbent material, and placing the substrate in a location where the presence of radon is being determined, and, in step (i), placing the capsule composition and esterase in contact with each other on said regions containing the absorbent material and said regions not containing the absorbent material after the absorbent material is provided sufficient time to absorb radon; proceeding with steps (ii); and in step (iii), determining the presence or extent of leakage of the solution in regions containing the absorbent material and comparing this result to regions not containing the absorbent material to determine if regions containing the absorbent material exhibit leakage or a higher leakage of the solution compared to regions not containing the absorbent material.

22. The method of claim 20, wherein said absorbent material comprises a cryptophane.

23. The method of claim 12, wherein, in step (i), said capsule composition and esterase are present on a sheet substrate material when placed in a location where the presence of alpha particle radiation is being determined.

24. The method of claim 23, wherein an alpha radiation blocking layer is positioned over a portion of the capsule composition and esterase when said sheet substrate material coated with the capsule composition and esterase is placed in a location where the presence of alpha particle radiation is being determined, and comparing the presence or extent of leakage of the solution in regions covered by said alpha radiation blocking layer and regions not covered by said alpha radiation blocking layer to determine if regions not covered by said alpha radiation blocking layer exhibit leakage or a higher leakage of the solution compared to regions covered by said alpha radiation blocking layer.

* * * * *